US010806695B2

(12) United States Patent
Chung et al.

(10) Patent No.: US 10,806,695 B2
(45) Date of Patent: *Oct. 20, 2020

(54) PROTEIN STABILIZING FACTORS

(71) Applicant: Bloodworks, Seattle, WA (US)

(72) Inventors: Dominic W. Chung, Seattle, WA (US);
Jose Aron Lopez, Seattle, WA (US);
Minhua Ling, Kenmore, WA (US);
Junmei Chen, Seattle, WA (US);
Xiaoyun Fu, Kenmore, WA (US)

(73) Assignee: BLOODWORKS, Seattle, WA (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/373,390

(22) Filed: Apr. 2, 2019

(65) Prior Publication Data

US 2019/0216723 A1 Jul. 18, 2019

Related U.S. Application Data

(62) Division of application No. 14/442,387, filed as application No. PCT/US2013/069545 on Nov. 12, 2013, now Pat. No. 10,441,531.

(60) Provisional application No. 61/830,618, filed on Jun. 3, 2013, provisional application No. 61/724,882, filed on Nov. 9, 2012.

(51) Int. Cl.
| | | |
|---|---|---|
| *A61K 38/00* | (2006.01) | |
| *A61K 9/00* | (2006.01) | |
| *C07K 14/755* | (2006.01) | |
| *A61L 29/08* | (2006.01) | |
| *A61L 29/04* | (2006.01) | |
| *A61L 31/14* | (2006.01) | |
| *A61L 31/16* | (2006.01) | |
| *A61L 31/10* | (2006.01) | |
| *C07K 14/775* | (2006.01) | |
| *A61L 29/14* | (2006.01) | |
| *A61L 29/16* | (2006.01) | |
| *A61K 47/42* | (2017.01) | |

(52) U.S. Cl.
CPC ............ *A61K 9/0019* (2013.01); *A61K 47/42* (2013.01); *A61L 29/048* (2013.01); *A61L 29/085* (2013.01); *A61L 29/143* (2013.01); *A61L 29/16* (2013.01); *A61L 31/10* (2013.01); *A61L 31/143* (2013.01); *A61L 31/16* (2013.01); *C07K 14/755* (2013.01); *C07K 14/775* (2013.01); *A61K 38/00* (2013.01); *A61L 2300/424* (2013.01); *A61L 2400/18* (2013.01); *Y02A 50/411* (2018.01)

(58) Field of Classification Search
None
See application file for complete search history.

(56) References Cited

U.S. PATENT DOCUMENTS

| 4,379,085 A | 4/1983 | Williams et al. |
|---|---|---|
| 6,372,716 B1 | 4/2002 | Bush et al. |
| 6,423,830 B1 | 7/2002 | Winge et al. |
| 7,959,659 B2 | 6/2011 | Ding |
| 8,623,352 B2 | 1/2014 | Matthiessen et al. |
| 2005/0175666 A1 | 8/2005 | Ding |
| 2007/0232539 A1 | 10/2007 | Kilpatrick et al. |
| 2013/0288387 A1 | 10/2013 | Blancher et al. |

FOREIGN PATENT DOCUMENTS

| EP | 0199992 B1 | 8/2006 |
|---|---|---|
| WO | WO2005068020 | 7/2005 |
| WO | WO2011006994 | 1/2011 |

OTHER PUBLICATIONS

Blood Buffers 2019 12 Pages (Year: 2019).*
Andrade and Hlady, "Plasma protein adsorption: the big twelve." Annals of the New York Academy of Sciences, vol. 516, No. 1, 1987, pp. 158-172.
Bonnefoy, "Thrombospondin-1 controls vascular platelet recruitment and thrombus adherence in mice by protecting (sub)endothelial VWF from cleavage by ADAMTS13," Blood, vol. 107, No. 3, 2006, pp. 955-964.
Office Action dated Apr. 24, 2017 in Canadian Application No. 2,890,848, 5 pages.
Office Action dated May 17, 2018 in Canadian Application No. 2,890,848, 5 pages.
Chung, Dominic, Curriculum Vitae, 2018, 11 pages.
Davidson and Thompson, "The structure of apolipoprotein A-I in high density lipoproteins," J. Biol. Chem., vol. 282, No. 31, 2007, pp. 22249-22253.
Fay, et al., "Human factor VIIIa subunit structure. Reconstruction of factor VIIIa from the isolated A1/A3-C1-C2 dimer and A2 subunit," J. Biol.. Chem., vol. 266, No. 14, 1991, pp. 8957-8962.
Furlan, "Von Willebrand factor: molecular size and functional activity," Ann. Hematol., vol. 72, No. 6, 1996, pp. 341-348.
Gonzalez-Montalban, et al., "Recombinant protein solubility—does more mean better?" Nat. Biotech., vol. 25, No. 7, 2007, 3 pages.

(Continued)

*Primary Examiner* — Thomas S Heard (74) *Attorney, Agent, or Firm* — Lee & Hayes PC; C. Rachal Winger; Thu Nguyen (57) ABSTRACT

Compositions and methods are described for preventing or reducing protein loss due to protein aggregation, denaturation, and absorption to surfaces. Also described are compositions and methods for preventing or reducing the fouling or clogging of medical devices that come into contact with blood, such as catheters. Also described are methods to treat diseases caused by activation of the microvasculature.

19 Claims, 8 Drawing Sheets

Specification includes a Sequence Listing.

(56) References Cited

OTHER PUBLICATIONS

Grillo, et. al., "Conformational Origin of the Aggregation of Recombinant Human Factor VIII", American Chemical Society, Published on Dec. 20, 2000, Biochemistry 2001, vol. 40, pp. 586-595.

Grunewald, et al., "Absence of compensatory platelet activation in patients with severe haemophilia, but evidence for a platelet collagen-activation defect," Platelets, vol. 13, No. 8, 2002, pp. 451-458.

Guo, et al., "Surface Properties of Heat-Induced Soluble Soy Protein Aggregates of Different Molecular Masses," J. Food. Science, vol. 80, No. 2, 2015, 9 pages.

Horton, et al., "Engineering hybrid genes without the use of restriction enzymes: gene splicing by overlap extension" Gene, vol. 77, No. 1, 1989, pp. 61-68.

Jain, et al., "Does Heparin Coating Improve Patency or Reduce Infection of Tunneled Dialysis Catheters?" Clinical Journal of the American Society of Nephrology, vol. 4, 2009, pp. 1787-1790.

Kaufman, et al., "Improved vectors for stable expression of foreign genes in mammalian cells by use of the untranslated leader sequence from EMC virus," Nucl. Acids Res., vol. 19, No. 16, 1991, pp. 4485-4490.

Khoo, et al., "Prevention of Low Density Lipoprotein Aggregation by High Density Lipoprotein or Apolipoprotein A-1," J. Lipid Res., vol. 31, No. 4, 1990, pp. 645-652.

Kokame, et al., "FRETS-VWF73, a first fluorogenic substrate for ADAMTS13 assay," Br. J. Haematol., vol. 129, No. 1, 2005, pp. 93-100.

Lankhof, et al., "Recombinant vWF type 2A mutants R834Q and R834W show a defect in mediating platelet adhesion to collagen, independent of enhanced sensitivity to a plasma protease," Thromb. Haemost., vol. 81, No. 6, 1999, pp. 976-983.

Levy, et al., "Mutations in a member of the ADAMTS gene family cause thrombotic thrombocytopenic purpura," Nature, vol. 413, No. 6855, 2001, pp. 488-494.

Lindahl, et al. Proteoglycans and Sulfated Glycosaminoglycans. 2017. In: Varki A, Cummings RD, Esko JD, et al., editors. Essentials of Glycobiology [Internet]. 3rd edition. Cold Spring Harbor (NY): Cold Spring Harbor Laboratory Press; 2015-2017. Chapter 17. Available from: https://www.ncbi.nlm.nih.gov/books/NBK453033/ doi: 10.1101/glycobiology.3e.017.

Linton, et al., "The Role of Lipids and Lipoproteins in Atherosclerosis," [Updated Dec. 24, 2015]. In: De Groot LJ, Chrousos G, Dungan K, et al., editors. Endotext [Internet]. South Dartmouth (MA): MDText.com, Inc.; 2000-. Available from: https://www.ncbi.nlm.nih.gov/books/NBK343489/, 97 pages.

Lopez and Dong, "Shear stress and the role of high molecular weight von Willebrand factor multimers in thrombus formation," Blood Coagul. Fibrinolysis, vol. 16, Suppl 1, 2005, pp. S11-S16.

Lund-Katz and Phillips, "High density lipoprotein structure-function and role in reverse cholesterol transport," Subcell. Biochem., vol. 51, 2010, pp. 183-227.

Lusher, et al. "Recombinant Factor VIII for the Treatment of Previously Untreated Patients with Hemophilia A," New England Journal of Medicine, vol. 328, No. 7, 1993, pp. 453-459.

Mize, et al. "Regulated expression of active biotinylated G-protein coupled receptors in mammalian cells," Protein Expr. Purif., vol. 57, No. 2, 2008, pp. 280-289.

NCBI Blast: APOB_HUMAN Apolipoprotein B-100, 9 pages.

Nishimura, et al, "Human Factor IX Has a Tetrasaccharide O-Glycosidically Linked to Serine 61 through the Fucose Residue," J. Biol. Chem., vol. 267, No. 25, 1996, pp. 17520-17525.

Noma, et al., "Elastin—Lipid Interaction in the Arterial Wall," Atherosclerosis, vol. 38, No. 3-4, 1981, pp. 373-382.

Norata, et al. "Molecular Mechanisms Responsible for the Anti-Inflammatory and Protective Effect of HDL on the Endothelium," Vascular Health and Risk Management, vol. 1, No. 2, 2005, pp. 119-129.

Nossent, et al., "von Willebrand factor and its propeptide: the influence of secretion and clearance on protein levels and the risk of venous thrombosis," J. Thromb. Haemost., vol. 4, No. 12, 2006, pp. 2556-2562.

Office Action for U.S. Appl. No. 14/442,387, dated Jun. 27, 2018, Chung, "Protein Stabilizing Factors", 11 pages.

Office Action dated May 26, 2016 in Canadian Application No. 2,890,848, 5 pages.

Ono, et al., "Severe secondary deficiency of von Willebrand factor-cleaving protease (ADAMTSI3) in patients with sepsis-induced disseminated intravascular coagulation: its correlation with development of renal failure," Blood, vol. 107, No. 2, 2006, pp. 528-534.

Rabe, et al., "Understanding protein adsorption phenomena at solid surfaces," Adv. Colloid Interface Sci., vol. 162, 2011, pp. 87-106.

Rock, et al., "Acquired von Willebrand factor deficiency during high-dose infusion of recombinant factor VIII," Br. J. Haematol., vol. 93, No. 3, 1996, pp. 684-687.

Ross, "Rous-Whipple Award Lecture—Atherosclerosis: A Defense Mechanism Gone Wrong," Am. J. Pathol., vol. 143, No. 4, 1993, 17 pages.

Ryan and Foegeding, "Formulation of soluble whey protein aggregates and their stability in beverates," Food Hydrocolloids, vol. 43, 2015, pp. 265-274.

Sadler, "Biochemistry and genetics of von Willebrand factor," Annu. Rev. Biochem., vol. 67, 1998, pp. 395-424.

Segrest, et al., "Structure of apolipoprotein B-100 in low density lipoproteins," J. Lipid Res., vol. 42, 2001, pp. 1346-1367.

Search Report and Written Opinion dated Aug. 9, 2014 in International Application No. PCT/US13/69545, 25 pages.

Thorell and Blomback, "Purification of the factor VIII complex," Thromb. Res., vol. 35, No. 4, 1984, pp. 431-450.

Tomokiyo, et al., "von Willebrand factor accelerates platelet adhesion and thrombus formation on a collagen surface in platelet-reduced blood under flow conditions," Blood, vol. 105, No. 3, 2005, pp. 1078-1084.

Toso and Camire, "Removal of B-domain sequences from factor V rather than specific proteolysis underlies the mechanism by which cofactor function is realized," J. Biol. Chem.,vol. 279, No. 20, 2004, pp. 21643-21650.

Tsai, "Molecular mechanisms in thrombotic thrombocytopenic purpura," Semin. Thromb. Hemost., vol. 30, No. 5, 2004, pp. 549-557.

Zheng, et al, "In vitro microvessels for the study of angiogenesis and thrombosis," PNAS, vol. 109, No. 24, 2012, pp. 9342-9347.

Zheng, et al., "Structure of von Willebrand factor-cleaving protease (ADAMTSI3), a metalloprotease involved in thrombotic thrombocytopenic purpura," J. Biol. Chem., vol. 276, No. 44, 2001, pp. 41059-41063.

The Canadian Office Action dated Mar. 28, 2019 for Canadian patent application No. 2890848, a counterpart foreign application of U.S. Appl. No. 14/442,387, 5 pages.

\* cited by examiner

|   |   |   |   |   |   |                    |
|---|---|---|---|---|---|--------------------|
| + | + | + | + | + | + | Purified plasma VWF |
| − | − | − | + | + | + | Boiled plasma      |
| − | − | + | − | − | + | EDTA (5 mM)        |
| 0 | 4 | 4 | 0 | 4 | 4 | Time (hr)          |

Component A is α₁ acid glycoprotein 1 (orosomucoid)

| Accession | Coverage | # PSMs | # Peptides | # AAs | MW [kDa] | calc. pI | Score | Description |
|---|---|---|---|---|---|---|---|---|
| IPI:IPI00884926.1 | 53.73 | 876 | 15 | 201 | 23.5 | 5.11 | 2677.42 | orosomucoid 1 precursor |
| IPI:IPI00020091.1 | 53.73 | 537 | 14 | 201 | 23.6 | 5.11 | 1651.09 | Alpha-1-acid glycoprotein 2 |
| IPI:IPI00021841.1 | 62.17 | 250 | 20 | 267 | 30.8 | 5.76 | 810.22 | Apolipoprotein A-I |

Component B is Apolipoprotein A1 (APOAI)

| Accession | Coverage | # PSMs | # Peptides | # AAs | MW [kDa] | calc. pI | Score | Description |
|---|---|---|---|---|---|---|---|---|
| IPI:IPI00021841.1 | 81.27 | 1986 | 38 | 267 | 30.8 | 5.76 | 6664.51 | Apolipoprotein A-I |
| IPI:IPI00745872.2 | 71.26 | 645 | 49 | 609 | 69.3 | 6.28 | 1954.66 | Isoform 1 of Serum albumin |
| IPI:IPI00304273.2 | 71.46 | 432 | 36 | 396 | 45.4 | 5.38 | 1502.89 | Apolipoprotein A-IV |

Component C is transthyretin (prealbumin)

| Accession | Coverage | # PSMs | # Peptides | # AAs | MW [kDa] | calc. pI | Score | Description |
|---|---|---|---|---|---|---|---|---|
| IPI:IPI00022432.1 | 69.39 | 270 | 10 | 147 | 15.9 | 5.76 | 889.50 | Transthyretin |

Fluid-phase VWF attaching to transluminal fiber

Apo AI blocks soluble VWF binding to ULVWF fibers

Total VWF
Apo-AI
Fluid phase VWF
Nuclei

SEQUENCE LISTING

```
<160> NUMBER OF SEQ ID NOS: 2

<210> SEQ ID NO 1
<211> LENGTH: 897
<212> TYPE: DNA
<213> ORGANISM: Homo sapiens

<400> SEQUENCE: 1
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccaacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag gagatggagc tctaccgcca gaaggtggag ccgctgcgcg     480
cagagctcca agagggcgcg cgccagaagc tgcacgagct gcaagagaag ctgagcccac     540
tgggcgagga gatgcgcgac cgcgcgcgcg cccatgtgga cgcgctgcgc acgcatctgg     600 cccctacag cgacgagctg cgccagcgct tggccgcgcg ccttgaggct ctcaaggaga     660
acggcggcgc cagactggcc gagtaccacg ccaaggccac cgagcatctg agcacgctca     720
gcgagaaggc caagcccgcg ctcgaggacc tccgccaagg cctgctgccc gtgctggaga     780
gcttcaaggt cagcttcctg agcgctctcg aggagtacac taagaagctc aacacccagt     840
gaggcgcccg ccgccgcccc ccttcccggt gctcagaata aacgtttcca aagtggg      897
```

```
<210> SEQ ID NO 2
<211> LENGTH: 267
<212> TYPE: PRT
<213> ORGANISM: Homo sapiens

<400> SEQUENCE: 2

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
                35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

PROTEIN STABILIZING FACTORS

CROSS-REFERENCE TO RELATED APPLICATIONS

This application is a divisional of U.S. patent application Ser. No. 14/442,387, filed May 12, 2015, which is a U.S. National Phase application based on PCT/US2013/069545, filed Nov. 12, 2013, which claims the benefit of priority to U.S. Provisional Patent Application No. 61/830,618, filed Jun. 3, 2013, and to U.S. Provisional Patent Application No. 61/724,882, filed Nov. 9, 2012, each of which is incorporated herein by reference in its entirety as if fully set forth herein.

STATEMENT OF GOVERNMENT SUPPORT

This invention was made with Government support of Grant No. R01HL091153 and R21HL098672, awarded by the National Institutes of Health. The Government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is B212-0025USC1 Sequence Listing_ST25.txt. The text file is 4 KB, was created on Nov. 12, 2013, and is being submitted electronically via EFS-Web.

FIELD

The present disclosure relates to the field of protein stability and reduction of protein loss by adsorption to surfaces. In particular, the present disclosure provides compositions and methods for reducing protein aggregation, denaturation, and adsorption to surfaces that result in protein loss. Also provided are methods to treat diseases caused by activation of the microvasculature.

BACKGROUND

The development and production of therapeutic proteins and peptides is rapidly expanding in the pharmaceutical industry. Currently, there are many approved monoclonal antibody and protein therapeutics that have been approved or which are in clinical studies. This number will undoubtedly increase in the upcoming years. During the manufacturing process, transport, and storage, a protein therapeutic can be subjected to a variety of conditions that promote protein aggregation, denaturation, and adsorption that will result in loss of precious material. To protect against such degradation, protein therapeutics are usually formulated with excipients to provide the product with an acceptable shelf life for storage and shipping.

A related problem that can result from protein aggregation, denaturation, and adsorption is the "fouling" of surfaces that come into contact with blood, such as intravenous and intraarterial catheters. Adhesion of proteineaous material and the formation of biofilm on indwelling medical devices can contribute to catheter-related infections and are a major cause of patient morbidity and mortality, often resulting in premature catheter removal or replacement and an increase in costs and use of resources in this medical setting.

A need exists in the art for improved compositions and methods for preventing aggregation, denaturation, and adsorption of proteins. The present invention fulfills these and other needs.

SUMMARY

The present disclosure provides in a first aspect, a method of preventing loss of a protein by adsorption to a surface or protein self-association, the method comprising maintaining the protein in the presence of an amount of ApoA-1 and/or HDL sufficient to prevent adsorption of the protein to a surface or protein self-association.

In various embodiments of the first aspect, the protein is a recombinant purified protein or a native protein. In some embodiments of this aspect, the protein is VWF, Factor VIII, Factor IX, or ADAMTS13. In further embodiments, the concentration of ApoA-1 is at least 40 µg/mL, and the concentration of HDL is at least 80 µg/mL.

In a second aspect, the present disclosure provides a method of preventing fouling or clogging of a medical device, the method comprising treating the surfaces of said device with an amount of ApoA-1 and/or HDL sufficient to prevent fouling or clogging of the device.

In various embodiments of the second aspect, the medical device is an intravenous catheter, intraarterial catheter, or ventricular assist device.

In other embodiments of the second aspect, the medical device is a central venous catheter, a peripheral intravenous catheter, an arterial catheter, a Swan-Ganz catheter, a hemodialysis catheter, an umbilical catheter, a percutaneous non-tunneled silicone catheter, a cuffed tunneled central venous catheter or a subcutaneous central venous port.

In a third aspect, the present disclosure provides a method for controlling the fouling or clogging of a medical device, the method comprising providing to said device a composition comprising ApoA-1 and/or HDL sufficient to prevent protein adsorption to a surface or protein self-association.

In various embodiments of the third aspect, the composition is a transport fluid or flush solution.

In other embodiments of the third aspect, the medical device is an intravenous catheter, intraarterial catheter, or ventricular assist device.

In further embodiments of the third aspect, the medical device is a central venous catheter, a peripheral intravenous catheter, an arterial catheter, a Swan-Ganz catheter, a hemodialysis catheter, an umbilical catheter, a percutaneous non-tunneled silicone catheter, a cuffed tunneled central venous catheter or a subcutaneous central venous port.

In a fourth aspect, the present disclosure provides a composition comprising a protein and an amount of ApoA-1 and/or HDL sufficient to prevent adsorption of the protein to a surface or loss of the protein due to self-association.

In an embodiment of the fourth aspect, the surface is a container holding the composition. In a further embodiment, the surface is glass or plastic.

In another embodiment of the fourth aspect, the protein is a therapeutic protein. In other embodiments, the protein is VWF, Factor VIII, Factor IX, or ADAMTS13.

In a fifth aspect, the present disclosure provides a medical device coated with a composition comprising an amount of ApoA-1 and/or HDL in an amount sufficient to prevent fouling or clogging of the device by proteins or the adherence of proteins to the walls of the device.

In an embodiment of the fifth aspect, the medical device is an intravenous catheter, intraarterial catheter, or ventricular assist device.

In another embodiment of the fifth aspect, the medical device is a central venous catheter, a peripheral intravenous catheter, an arterial catheter, a Swan-Ganz catheter, a hemodialysis catheter, an umbilical catheter, a percutaneous non-tunneled silicone catheter, a cuffed tunneled central venous catheter or a subcutaneous central venous port.

In a sixth aspect, the present disclosure provides a method of treatment of a disease caused by activation of the microvasculature comprising administration to a subject in need thereof an amount of Apo AI and/or HDL or a fragment thereof, in an amount effective to reduce or prevent the disease.

In various embodiments of the sixth aspect, the disease is TTP, HUS, sepsis, malaria, or sickle cell disease. In other embodiments of the sixth aspect, the administration decreases VWF release, modulates fiber self-association, and/or prevents association of fluid-phase VWF with endothelial VWF.

BRIEF DESCRIPTION OF THE FIGURES

FIGS. 2A, 2B. Macromolecules in boiled plasma stabilized and prevented adsorption of purified recombinant A1A2A3 fragment of VWF to surfaces.

FIGS. 3A, 3B. Macromolecules in boiled plasma stabilized and prevented adsorption of purified recombinant biotinylated VWF to surfaces. Purified recombinant biotinylated VWF was incubated without (lane 1) and with (lane 2) boiled plasma in 10 mM HEPES, 2 mM $CaCl_2$ at 37° C. overnight. Recombinant VWF remaining in solution (FIG. 3A) and VWF bound to surface and eluted by SDS (FIG. 3B) was analyzed by reduced SDS-PAGE, transferred onto PVDF membrane, and visualized by a streptavidin-HRP conjugated.

FIG. 4. SDS-PAGE analysis of proteins in boiled plasma. Lane 1, boiled plasma, 20 µg. Lane 2, a1 acid glycoprotein, 5 µg. Lane 3, apolipoprotein A-1, 5 µg. Lane 4, prealbumin, 5 µg. After electrophoresis in a 4%-20% polyacrylamide gel, separated proteins were stained with GelCode Blue (Thermo Scientific).

FIGS. 6A, 6B. Apolipoprotein A-1 and HDL prevented purified recombinant biotinylated VWF from adsorption to surfaces. Purified recombinant VWF (12 µg/mL) was incubated without and with various proteins and VWF remaining in solution (FIG. 6A) and bound to the tube surface eluted in 4% CHAPS (FIG. 6B) were analyzed by SDS-PAGE after reduction and western blot onto nitrocellulose membrane probed with streptavidin-HRP. Lane 1, purified recombinant VWF; lane 2, VWF incubated in absence of added protein; lane 3, VWF with apolipoprotein A-1 (40 µg/mL); lane 4, VWF with HDL (80 µg/mL); lane 5, VWF with boiled plasma (40 µg/mL); lane 6, VWF with a1 acid glycoprotein, (40 µg/mL); lane 7, VWF with prealbumin (40 µg/mL); lane 8, VWF with bovine serum albumin (40 µg/mL).

FIGS. 7A, 7B. Apolipoprotein A-1 and HDL prevented purified recombinant biotinylated ADAMTS13 from adsorption to surfaces. SDS-PAGE and western blot analysis of purified recombinant ADAMTS13 after 16 hr incubation with various proteins.

FIGS. 8A-8C. Apolipoprotein A-1 prevented association of purified recombinant biotinylated A1A2A3 in the fluid phase to surface-bound recombinant biotinylated VWF. SDS-PAGE and western blot analysis of biotinylated proteins after exposure to surface.

DETAILED DESCRIPTION

The present disclosure was motivated by the observation that while the blood borne proteins, VWF and ADAMTS13, are stable in plasma, purified VWF and ADAMTS13 are labile and readily lose activity upon dilution and exposure to surfaces. This suggested to the present inventors that factors present in plasma serve to stabilize these proteins. As disclosed herein, further investigation resulted in the identification of factors that stabilize proteins and reduce loss by preventing aggregation, denaturation, and adsorption of proteins to surfaces, using VWF and ADAMTS13 as model proteins.

In particular, the present inventors have surprisingly found that among the factors that have stabilizing activity are the proteins, ApoA-1 or HDL, which as shown herein, are able to protect VWF and other proteins from attaching to surfaces, including plastic. In the case of VWF, these factors also prevent self-association. Accordingly, these factors can be used to stabilize VWF, or other highly purified recombinant proteins useful as drugs, such as factors VIII and IX, and ADAMTS13, and any other proteins that can be shown to be stabilized by ApoA-1 and/or HDL.

Additionally, because of these properties, ApoA-1 and HDL may be used as additives to prevent the "fouling" of surfaces that come in contact with blood, such as intravenous and intraarterial cathethers, and other devices, such as ventricular assist devices.

Moreover, the present inventors have investigated the effect of ApoA-1 and HDL on the interaction of VWF with endothelial microvessel surfaces. Based on these studies, methods for the treatment of diseases caused by activation of the microvasculature are also presented.

The descriptions of various aspects of the invention are presented for purposes of illustration, and are not intended to be exhaustive or to limit the invention to the forms disclosed. Persons skilled in the relevant art can appreciate that many modifications and variations are possible in light of the aspect teachings.

It must be noted that, as used in the specification and the appended claims, the singular forms "a," "an" and "the" include plural referents unless the context clearly dictates otherwise. The definition of standard terminology can be found in reference works, including Sambrook et al., Molecular Cloning, A Laboratory Manual (1989) and Ausubel et al., Short Protocols in Molecular Biology (1999) 4th Ed., John Wiley & Sons, Inc. (as well as the complete version of Current Protocols in Molecular Biology). The practice of the present disclosure will employ, unless otherwise indicated, conventional methods of mass spectroscopy, protein chemistry, biochemistry, recombinant DNA techniques and pharmacology, all of which are within the skill of those in the art.

Von Willebrand Factor (VWF)

VWF is a plasma glycoprotein required for primary hemostasis. As an extracellular adapter molecule it mediates the adhesion of platelets to subendothelial collagen of a damaged blood vessel and platelet-platelet interactions in high shear-rate conditions. The concentration of mature VWF in plasma is approximately 10 μg/mL, and its half life is about 12 hours (Tomokiyo et al., Blood, 105:1078-1084 (2005); Nossent et al., J Thromb Haemost, 4:2556-2562 (2006)). VWF is synthesized in endothelial cells, where it is either secreted constitutively or stored in Weibel-Palade bodies for secretion upon stimulation, as well as in megakaryocytes, where it is stored in α-granules that later are partitioned into platelets (Ono et al., Blood, 107:528-534 (2006)). Subsequent to the synthesis in the form of a precursor protein, VWF undergoes a number of intracellular processing steps. Building blocks of the VWF multimer are initially generated in a dimeric form by formation of a disulfide bond near the C-terminus. By generation of disulfide bonds near the N-termini, the protein multimerizes to a gigantic protein with a molecular mass ranging over 3 orders of magnitude to more than 20,000 kDa (Sadler, Annu Rev Biochem, 67:395-424 (1998)). Through the process of self-association subsequent to its secretion, VWF can show the extraordinary length of several millimeters.

The pro-coagulant activity of VWF exhibits a non-linear function of size, since the larger the multimer, the more effective it is in promoting platelet adhesion exhibiting a critical effect on its function (Furlan, Ann Hematol, 72:341-348 (1996)). However, under shear stress conditions in the circulation the protein emerges more vulnerable to proteolytic digestion by ADAMTS13 (Lopez et al., Blood Coagul Fibrinolysis, 16 Suppl 1:S11-6 (2005)).

Regulation of VWF multimer composition in plasma is mediated by two major cleaving events: first, ADAMTS13 proteolytically cleaves the A2 domain of each VWF monomer and second, thrombospondin-1 reduces the disulfide bonds interlinking VWF multimers (Tsai, Semin Thromb Hemost, 30:549-557 (2004)). In contrast to an irreversible fragmentation of VWF by ADAMTS13, the activity of thrombospondin-1 can regulate VWF size reversibly employing a reductase activity. Thrombospondin-1 is crucially involved in the predominant VWF cleavage by ADAMTS13 due to competition with ADAMTS13 for binding to the VWF A3 domain (Bonnefoy et al., Blood, 107: 955-964 (2006)).

The term "VWF" or "recombinant VWF" or "rVWF" can be used interchangeably herein and refers to the von Willebrand factor polypeptide and multimers.

The term "VWF cleavage fragment" or "VWF fragments" or "VWF cleavage products" are used interchangeably herein and refer to fragments of VWF which are derived from VWF, including those generated by protease cleavage. In various aspects, the protease cleaving VWF is ADAMTS13. ADAMTS13, also called VWF-cleaving protease (VWFCP), is a zinc-containing metalloprotease enzyme that cleaves VWF. ADAMTS13 is secreted into blood and degrades large VWF multimers, decreasing their hemostatic activity. ADAMTS13 contains of multiple structural and functional domains, and these domains can participate in the recognition and binding of ADAMTS13 to VWF.

The terms "VWF multimers," "multimers," or "multimer forms" are used interchangeably herein. The ultra large VWF (ULVWF) multimers are cleaved by ADAMTS13 as they are secreted from endothelial cells. Thus, the terms "ADAMTS13 and "VWFCP" are used interchangeably.

ADAMTS13

The terms "ADAMTS13," "recombinant ADAMTS13," and "rADAMTS13" can be used interchangeably and refer to a protein encoded by ADAMTS13, a gene responsible for the familial form of thrombotic thrombocytopenic purpura (TTP). Structural details and sequence information on ADAMTS13 can be found in Zheng et al. (Zheng et al., J Biol Chem, 276(44):41059-41063 (2001)), and said structure and sequence are hereby incorporated by reference. ADAMTS13 has been identified as a unique member of the metalloproteinase gene family, ADAM (a disintegrin and metalloproteinase). ADAMTS family members are distinguished from ADAMs by the presence of one or more thrombospondin 1-like (TSP1) domain(s) at the C-terminus and the absence of the EGF repeat, transmembrane domain and cytoplasmic tail typically observed in ADAM metalloproteinases. ADAMTS13 is known to possess VWF-cleaving protease activity.

The plasma ADAMTS13 in healthy individuals ranges from 0.5 mg to 1 mg per liter (Grunewald et al., Platelets, 13:451-458 (2002); Rock et al., Br J Haematol, 93:684-687 (1996)). ADAMTS13 consists of metalloprotease, disintegrin, first thrombospondin type 1 (TSP-1) repeat, Cys-rich and spacer domains (Zheng et al., J Biol Chem, 276(44): 41059-41063 (2001); Levy et al., Nature, 413:488-494 (2001)). The C-terminus of ADAMTS13 has additional TSP1 repeats and two CUB domains. Previous studies have shown that the N-terminus of ADAMTS13 is necessary and sufficient for recognition and cleavage of denatured multimeric VWF (Fay et al., J Biol Chem, 266:8957-8962 (1991); Horton et al., Gene, 77:61-68 (1989); Kaufman et al., Nucl Acids Res, 19:4485-4490 (1991)) or peptide substrate (GST-VWF73 or FRETS-VWF73) (Fay et al., J Biol Chem, 266:8957-8962 (1991); Kokame et al., Br J Haematol, 129:93-100 (2005)). More recent studies have demonstrated that the spacer domain of ADAMTS13 binds the exosite (E-1660 APDLVLQR-1668) near the C-terminus of the VWF-A2 domain (Toso et al., J Biol Chem, 279: 21643-21650 (2004); Lankhof et al., Thromb Haemost, 81:976-983 (1999)). However, the role of the middle and distal C-terminal domains of ADAMTS13 in substrate recognition remains controversial.

Apolipoprotein A1 (ApoA-1)

Apolipoproteins are proteins that bind lipids to form lipoproteins. Apolipoprotein A-1 is the major protein component of high density lipoprotein (HDL) in plasma, with a molecular weight of approximately 28 kDa. Human ApoA-1 is a 243 amino acid protein. The sequence of ApoA-1 has been determined in a number of species and was found to be highly conserved, especially at the N-terminus. The crystal structure of Apo-A1 in a lipid-free state reveals an N-terminal anti-parallel four-helix bundle domain and a separate two-helix C-terminal domain. See, e.g., Davidson and Thompson, J. Biol. Chem., 282: 22249-22253 (2007) for a review of ApoA-1 structure and function.

An exemplary sequence of a human ApoA-1 (NCBI Reference Sequence: NM_000039.1) is shown below.

As used herein "ApoA-1" or "recombinant ApoA-1" or "r ApoA-1" can be used interchangeably and refers to Apolipoprotein A-1 polypeptide. Also included in the invention are fragments and peptides derived from ApoA-1, as well as drugs that mimic the function of ApoA-1.

High-Density Lipoprotein (HDL)

High-density lipoprotein (HDL) is the smallest of the five major groups of lipoproteins, which enable lipids like cholesterol and triglycerides to be transported within the bloodstream. In healthy individuals, about thirty percent of blood cholesterol is carried by HDL.

The conformation of ApoA-1 in discoidal and spherical HDL particles has been modeled to be organized as a double-belt in discoidal particles and as a trefoil in speherical particles. See, e.g., Lund-Katz and Phillips, Subcell. Biochem. 51: 183-227 (2010) for a review of HDL structure and function.

EXEMPLARY ASPECTS

Below are examples of specific aspects for carrying out the present disclosure. The examples are offered for illustrative purposes only, and are not intended to limit the scope of the present disclosure in any way. Efforts have been made to ensure accuracy with respect to numbers used (e.g.,

```
cDNA
                                                          (SEQ ID NO:1)
    1 agagactgcg agaaggaggt cccccacggc ccttcaggat gaaagctgcg gtgctgacct 61 tggccgtgct cttcctgacg gggagccagg ctcggcattt ctggcagcaa gatgaacccc 121 cccagagccc ctgggatcga gtgaaggacc tggccactgt gtacgtggat gtgctcaaag 181 acagcggcag agactatgtg tcccagtttg aaggctccgc cttgggaaaa cagctaaacc 241 taaagctcct tgacaactgg gacagcgtga cctccacctt cagcaagctg cgcgaacagc 301 tcggccctgt gacccaggag ttctgggata acctggaaaa ggagacagag ggcctgaggc 361 aggagatgag caaggatctg gaggaggtga aggccaaggt gcagccctac ctggacgact 421 tccagaagaa gtggcaggag gagatggagc tctaccgcca gaaggtggag ccgctgcgcg 481 cagagctcca agagggcgcg cgccagaagc tgcacgagct gcaagagaag ctgagcccac 541 tgggcgagga gatgcgcgac cgcgcgcgcg cccatgtgga cgcgctgcgc acgcatctgg 601 cccctacag cgacgagctg cgccagcgct tggccgcgcg ccttgaggct ctcaaggaga 661 acggcggcgc cagactggcc gagtaccacg ccaaggccac cgagcatctg agcacgctca 721 gcgagaaggc caagcccgcg ctcgaggacc tccgccaagg cctgctgccc gtgctggaga 781 gcttcaaggt cagcttcctg agcgctctcg aggagtacac taagaagctc aacacccagt 841 gaggcgcccg ccgccgcccc ccttccggt gctcagaata aacgtttcca aagtggg
```

```
Protein
                                                          (SEQ ID NO:2)
MKAAVLTLAVLFLTGSQARHFWQQDEPPQSPWDRVKDLATVYVDVLKDSGRDYVSQFEGSAL

GKQLNLKLLDNWDSVTSTFSKLREQLGPVTQEFWDNLEKETEGLRQEMSKDLEEVKAKVQPY

LDDFQKKWQEEMELYRQKVEPLRAELQEGARQKLHELQEKLSPLGEEMRDRARAHVDALRTH

LAPYSDELRQRLAARLEALKENGGARLAEYHAKATEHLSTLSEKAKPALEDLRQGLLPVLESFK

VSFLSALEEYTKKLNTQ
``` amounts, temperatures, etc.), but some experimental error and deviation should, of course, be allowed for.

Example 1

Methods and Materials

The following reagents were purchased from Sigma-Aldrich: high density lipoprotein (HDL), al acid glycoprotein (AGP), prealbumin, CHAPS, dithiothreitol (DTT), ethylenediamine tetraacetic acid (EDTA), HEPES, protease inhibitor cocktail. Apolipoprotein A-1 was from Molecular Innovations. Bovine serum albumin (BSA) was from Equitech-Bio Inc. Sodium dodecyl sulfate (SDS) was from BDH Biochemicals. Urea was from Gibco-BRL. Calcium chloride was from Baker. PVDF and Nitrocellulose membranes, gradient (4%-20%) polyacrylamide gels were from Bio-Rad. HRP conjugated antibody to human VWF was from Dako. Streptavidin-horse radish peroxidase conjugate (SA-HRP), and GelCode Blue were from Thermo Scientific. Immobilon Western HRP substrate peroxide solution, and Ultracel 10K centrifugal filter were from Millipore. HPC4-agarose was from Roche. The BCA protein determination kit was from Thermo Scientific. Serum-free FreeStyle 293 culture medium was from Life Technologies Corp.

Preparation of Purified Human Plasma VWF

Human plasma VWF was purified from cryoprecipitate according to the method of Thorell and Blomback (Thromb Res, 35:431-450, (1984)). Briefly, human cryoprecipitate was dissolved in citrate buffer (55 mM Na-citrate, pH 6.8), and fibrinogen was precipitated from the preparation by 2M glycine at 37° C. for 30 min. After removal of the precipitated fibrinogen by centrifugation (2,500×g, 30 min at 4° C.), the VWF in the supernatant was precipitated by the addition of NaCl to a final concentration of 1.55M. The precipitated VWF was collected by centrifugation (2,500×g, 30 min at 4° C.), dissolved in 2.5 mL of buffer (10 mM HEPES, 50 mM NaCl, pH 6.8), and chromatographed over a column of Sephacryl S500 (2.6 cm×93 cm, GE Healthcare) equilibrated in 10 mM HEPES, 50 mM NaCl, pH 6.8. Column fractions containing purified VWF were identified by ELISA, SDS-agarose gel electrophoresis, SDS-PAGE, and/or western blotting. The purified VWF was further concentrated by binding to Q Sepharose (1.5 cm×3 cm, GE Healthcare) in buffer containing 25 mM HEPES, 25 mM NaCl, 10 mM EDTA, pH 6.8. VWF was eluted in a concentrated form with 25 mM HEPES, 0.5M NaCl, pH 6.8. Purified VWF was stored at −80° C. until use.

Preparation of Boiled Human Plasma

Ten milliliters of normal human plasma anticoagulated with citrate was heated at 100° C. for 10 min. The heated plasma was frozen at −20° C. for 16 hr, thawed, broken in small pieces by a spatula, and centrifuged at 12,000×g for 20 min at 4° C. The supernatant (6 mL) was desalted over a column of Sephadex G25 (GE Healthcare) equilibrated in 10 mM HEPES, 2 mM CaCl$_2$), pH 7.4. The macromolecular fraction of boiled plasma (9 mL) devoid of material <10,000 Daltons was stored at −20° C. until use. The protein concentration of the desalted boiled plasma, determined with the BCA reagent using bovine serum albumin as standard, was 0.9 mg/mL.

Expression of Recombinant VWF

Recombinant human VWF, containing a C-terminal protein C epitope tag (PC-tag), and a biotin tag, was expressed as secreted multimers in stably transfected HEK293 cells that were also stably transfected and co-expressing human furin. Briefly, cDNA encoding residues Met1 to Lys2813 of VWF was inserted in frame in the vector and followed by an epitope tag derived from human protein C (PC tag) and a 13-residue biotin acceptor sequence (BioTag) (Mize et al., Protein Expr Purif, 57:280-289 (2008)) at the 3' end. Expression of recombinant VWF was under the control of a bidirectional doxycycline-inducible promoter, which also drives the expression of a bicistronic expression cassette encoding a secreted form of E. coli biotin ligase (BirA), and an enhanced green fluorescent protein (EGFP) reporter. The secreted form of biotin ligase enabled sequence-specific biotinylation of the BioTag in the secreted VWF, while cytoplasmic expression of EGFP, monitored by flow cytometry, and selected by fluorescence-activated cell sorting (FACS), enabled automated selection of transfected cells expressing biotinylated VWF. In order to obtain fully processed VWF without the propeptide, we co-transfected the VWF expression vector with a second vector that encoded human furin into HEK293 Tet-On cells using lipofactamine and stably transfected cells were selected and clonally expanded in the presence of puromycin.

Preparation of Purified Recombinant Biotinylated VWF

Stably transfected cells expressing recombinant VWF were grown to confluency, and expression of VWF was induced by the addition of doxycycline to a final concentration of 2 μg/mL. Serum-free FreeStyle 293 culture medium containing the secreted recombinant VWF multimers was collected and examined on SDS-agarose gels and by western blotting. The concentration of VWF antigen was typically 13-18 μg/mL measured by an ELISA, in which a polyclonal antibody to human VWF is coated on an ELISA plate as a capture antibody and an HRP-conjugated VWF antibody is used as a detection antibody. Recombinant VWF was purified by affinity chromatography over a monoclonal antibody (HPC4) column in the presence of calcium chloride. Cell culture medium containing recombinant VWF was thawed and calcium was added to a final concentration of 2 mM. One mL of culture medium was mixed with 0.2 mL of washed HPC4-agarose in a tube, and the mixture was mixed end-over-end at 4° C. for 16 hr, during which the biotinylated-VWF bound to the HPC4-agarose. The HPC4-agarose suspension was packed into a column, and washed with 5 mL of 10 mM HEPES, 2 mM CaCl$_2$, 100 mM NaCl, pH 7.4, followed by 10 mL of 10 mM HEPES, 2 mM CaCl$_2$, pH 7.4. The bound VWF was eluted with 1 mL of 10 mM HEPES, 10 mM EDTA, pH 7.4. Calcium was added to a final concentration of 12 mM and the purified biotinylated-VWF was used in stabilization studies within 1 hour of its purification. The concentration of purified recombinant VWF was ~12-13 μg/mL.

Preparation of Purified VWF A1A2A3 Fragment

The A1A2A3 region of VWF, encompassing Asp1261-Ile1878 of VWF, was expressed with an N-terminal biotin tag and a C-terminal PC tag with the pNBioSec (2) vector in stably transfected HEK293 Tet-On cells. Recombinant VWF A1A2A3 fragment was purified from cell culture medium by binding to and elution from HPC4-agarose as described above for recombinant VWF. Purified A1A2A3 fragment was used in stability studies within 1 hr of its purification.

Preparation of Purified Recombinant Human ADAMTS13

Recombinant ADAMTS13 was expressed with a N-terminal biotin tag and a C-terminal PC tag with the pNBioSec vector (Mize et al., Protein Expr Purif, 57:280-289 (2008)) in stably transfected HEK293 Tet-On cells. Serum-free FreeStyle 293 medium containing recombinant ADAMTS13 was concentrated tenfold by centrifugation in an Ultracel 10K centrifugal filter, and desalted over Sephadex G-25 to remove biotin and low molecular weight molecules. The concentrated recombinant ADAMTS13 preparation was treated with a mixture of protease inhibitors (Protease Inhibitor Cocktail, 1% v/v) and stored at −80° C. Recombinant ADAMTS13 was purified by chromatographed over a Superdex 200 HR column (1 cm×30 cm, GE Healthcare) equilibrated in 10 mM HEPES, 2 mM $CaCl_2$, pH 7.4. Purified ADAMTS13 was used in stabilization studies within 1 hour of its purification from the column.

Identification of Proteins by Mass Spectrometry

Proteins in boiled plasma were identified by nano-liquid chromatography-tandem mass spectrometry (nano-LC-MS/MS). Briefly, 5 μg proteins were reduced with 5 mM DTT, alkylated with 12.5 mM iodoacetamide, and digested overnight at 37° C. with trypsin (1:20, wt/wt, trypsin/total protein) in a buffer containing 50 mM ammonium bicarbonate and 5% acetonitrile. The resultant peptides were analyzed using nano-LC-MS/MS in the positive ion mode with a Thermo Scientific LTQ Orbitrap Velos mass spectrometer coupled to a Waters nanoACQUITY Ultra Performance LC system. MS/MS spectra were searched against the human protein database using Thermo Proteome Discoverer software with the SEQUEST search engine. Protein ID, sequence coverage, number of unique peptides and score listed in Table 1. Three major proteins in boiled plasma (FIG. 4, lane 1) are identified as al acid glycoprotein, apolipoprotein A-1, and transthyretin (prealbumin).

Protein Adsorption Assay

Purified plasma VWF, purified recombinant biotinylated VWF, purified recombinant biotinylated VWF A1A2A3 fragment, and purified recombinant biotinylated ADAMTS13 were diluted in 10 mM HEPES, 2 mM $CaCl_2$, and were incubated at 22° C. or 37° C. for 4 to 16 hr in 1.5 mL microfuge tubes. In a typical assay with VWF, 50 μL of VWF at 10 μg/mL was used. Proteins that were not adsorbed to tube surface and remained in solution were heated in 2% SDS at 100° C., and 10-12% of the samples were analyzed by SDS-1% agarose gel electrophoresis without reduction or by SDS-4%-15% gradient polyacrylamide gel electrophoresis after reduction with mercaptoethanol. The separated proteins on gels were transferred to PVDF or nitrocellulose membranes and the blots were blocked with 1% bovine serum albumin in TBST (50 mM Tris-HCl, pH 7.5, 150 mM NaCl, 0.1% Tween-20) for 30 minutes at room temperature, and probed with either an HRP-conjugated antibody to VWF or with a streptavidin-HRP conjugate diluted 1:10,000 in TBST containing 1% albumin. The membranes were washed for 15 min in three changes of TBST and incubated with the chemiluminescent HRP substrate Immobilon Western HRP substrate peroxide solution. The intensity of chemiluminescence was either recorded by exposure to X-ray films or captured on an ImageQuant 350 imaging system (GE Healthcare, Piscataway, N.J.) and quantitatively analyzed with the ImageQuant software. Proteins adsorbed to the tube surfaces were eluted either with 2% SDS or 4% CHAPS. Ten to twelve percent of the eluted fractions were analyzed by SDS-PAGE after reduction by mercaptoethanol and western blotting as described for the nonadsorbed fractions.

Example 2

Figure 1:
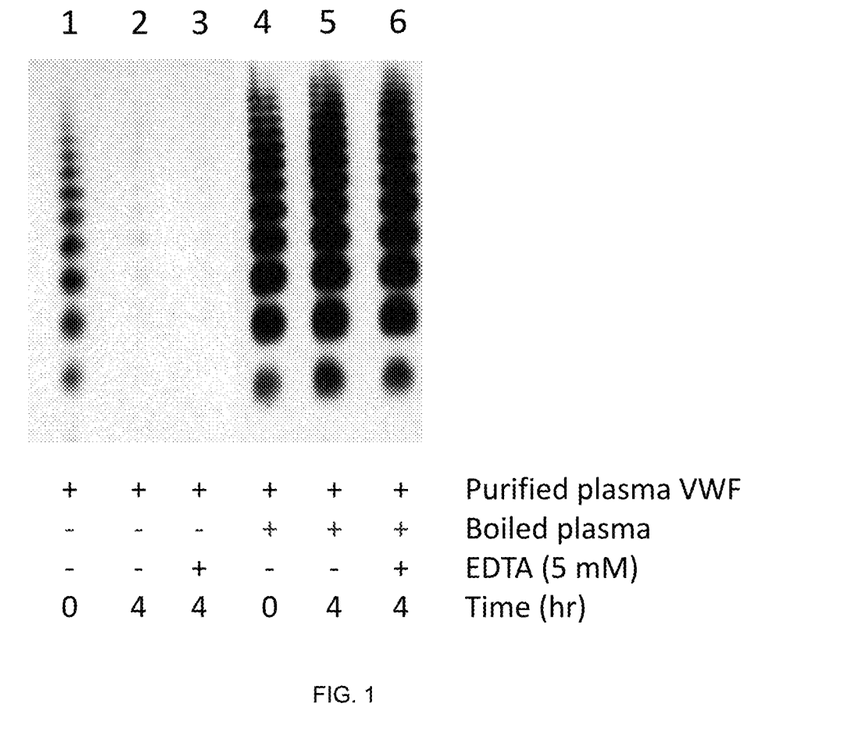
FIG. 1. Macromolecules in boiled plasma stabilized and prevented adsorption of purified plasma VWF to surfaces. Purified VWF was incubated with boiled plasma in 10 mM HEPES with 2 mM $CaCl_2$) at 37° C. VWF multimers were separated on a SDS-agarose gel, transferred onto PVDF membrane, and visualized by an HRP-conjugated VWF antibody.

Macromolecules in Boiled Plasma Stabilized and Prevented Adsorption of Purified Plasma VWF to Surfaces Purified VWF from human plasma was diluted in 10 mM HEPES, 2 mM $CaCl_2$), pH 7.4, and incubated at 37° C. for 4 hours. VWF multimers remaining in solution was analyzed by SDS-1% agarose gel electrophoresis, western blotting and visualization with an HRP-conjugated antibody to VWF. VWF multimers were nondetectable in solution (FIG. 1, lane 2), suggesting that the VWF had adsorbed to the tube surface. In contrast, when boiled plasma containing 90 μg/mL of protein was added to the purified plasma VWF during incubation, a substantial amount of the VWF remained in solution (FIG. 1, lane 5). These results showed that soluble macromolecules in boiled plasma stabilized VWF in solution and prevented its adsorption to the tube surfaces. Stabilization of VWF in solution or its adsorption to the tube surface was unaffected by the presence or absence of calcium ions (FIG. 1, lanes 3 and 6).

Example 3

Figure 2A:
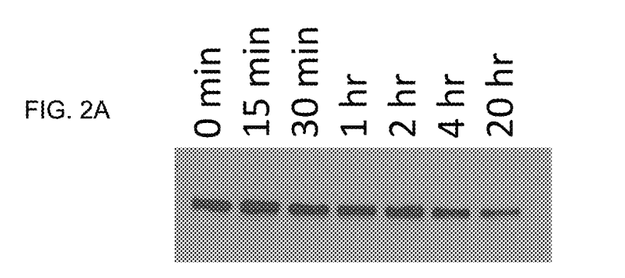
FIG. 2A. Purified A1A2A3 fragment of VWF remaining in solution after incubation in a tube for indicated duration.
Figure 2B:
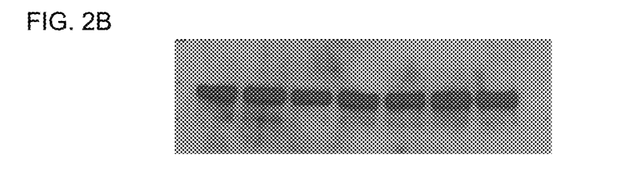
FIG. 2B. Purified A1A2A3 fragment of VWF remaining in solution after incubation with boiled plasma in a tube for the indicated duration.

Macromolecules in Boiled Plasma Stabilized and Prevented Adsorption of Purified Recombinant A1A2A3 Fragment of VWF to Surfaces Purified VWF A1A2A3 fragment was diluted in 10 mM HEPES, 2 mM $CaCl_2$), pH 7.4, and incubated at 22° C. for durations up to 20 hours. The A1A2A3 fragment is monomeric and does not multimerize into a collection of multimers as plasma VWF. As shown in FIG. 2A, the amount of A1A2A3 remaining in solution decreased with time. In contrast, the presence of macromolecules from boiled plasma (90 μg/mL) prevented the time-dependent decrease of A1A2A3 in solution (FIG. 2B). These results showed that soluble macromolecules in boiled plasma also stabilized the monomeric A1A2A3 fragment of VWF in solution and prevented its time-dependent adsorption to tube surfaces.

Example 4

Figure 3A:
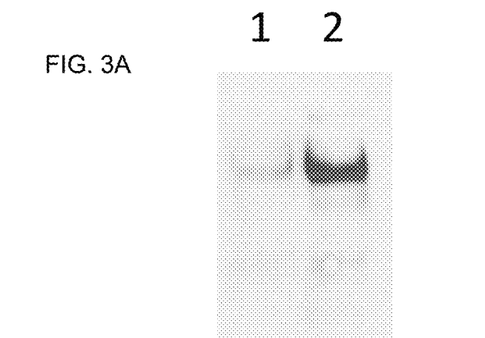
Figure 3B:
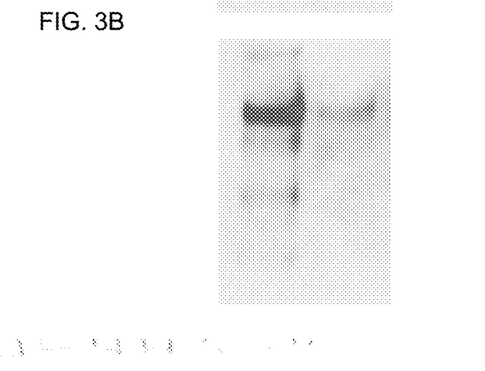

Macromolecules in Boiled Plasma Stabilized and Prevented Adsorption of Purified Recombinant Biotinylated VWF to Surfaces Purified recombinant VWF multimers, enzymatically biotinylated at the C-terminus of each subunit was diluted to 10 μg/mL in 10 mM HEPES, 2 mM $CaCl_2$), pH 7.4 and incubated at 22° C. for 16 hr in the presence or absence of boiled plasma. Ten percent of the VWF solutions were analyzed by SDS-4%-15% gradient polyacrylamide gel electrophoresis after reduction with mercaptoethanol. As shown in FIG. 3A, lane 1, absence of boiled plasma led to a substantial decrease of VWF in solution. However, a substantial amount of VWF remained in solution when boiled plasma (90 μg/mL) was present during the incubation (FIG. 3A, lane 2). Surface-bound VWF multimers were eluted from the tube surface by heating at 100° C. in 2% SDS for 2 min, and 10% of the eluted material was analyzed by SDS-4%-15% gradient polyacrylamide gel electrophoresis after reduction with mercaptoethanol. These results confirmed that a substantial amount of VWF had bound to and was recovered from the tube surface in the absence of boiled plasma (FIG. 3B, lane 1), while a small amount of VWF was recovered from the tube surface when boiled plasma was present during the incubation (FIG. 3B, lane 2). These results showed that similar to purified plasma VWF, purified recombinant biotinylated VWF multimers also adsorbed to the tube surface in the absence of boiled plasma, and at least a portion of the adsorbed material could be eluted from the tube surface by heating in 2% SDS.

Example 5

SDS-PAGE Analysis of Proteins in Boiled Plasma

Figure 4:
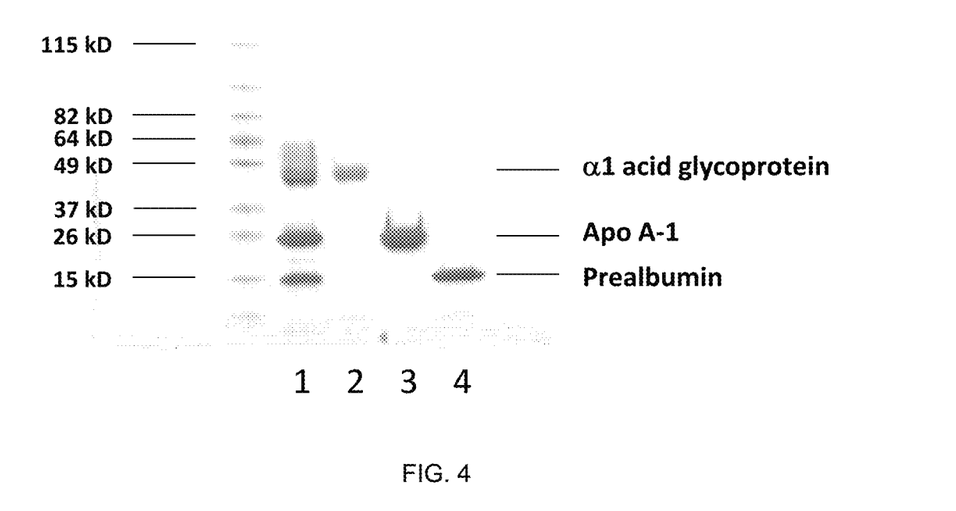
Figure 5:
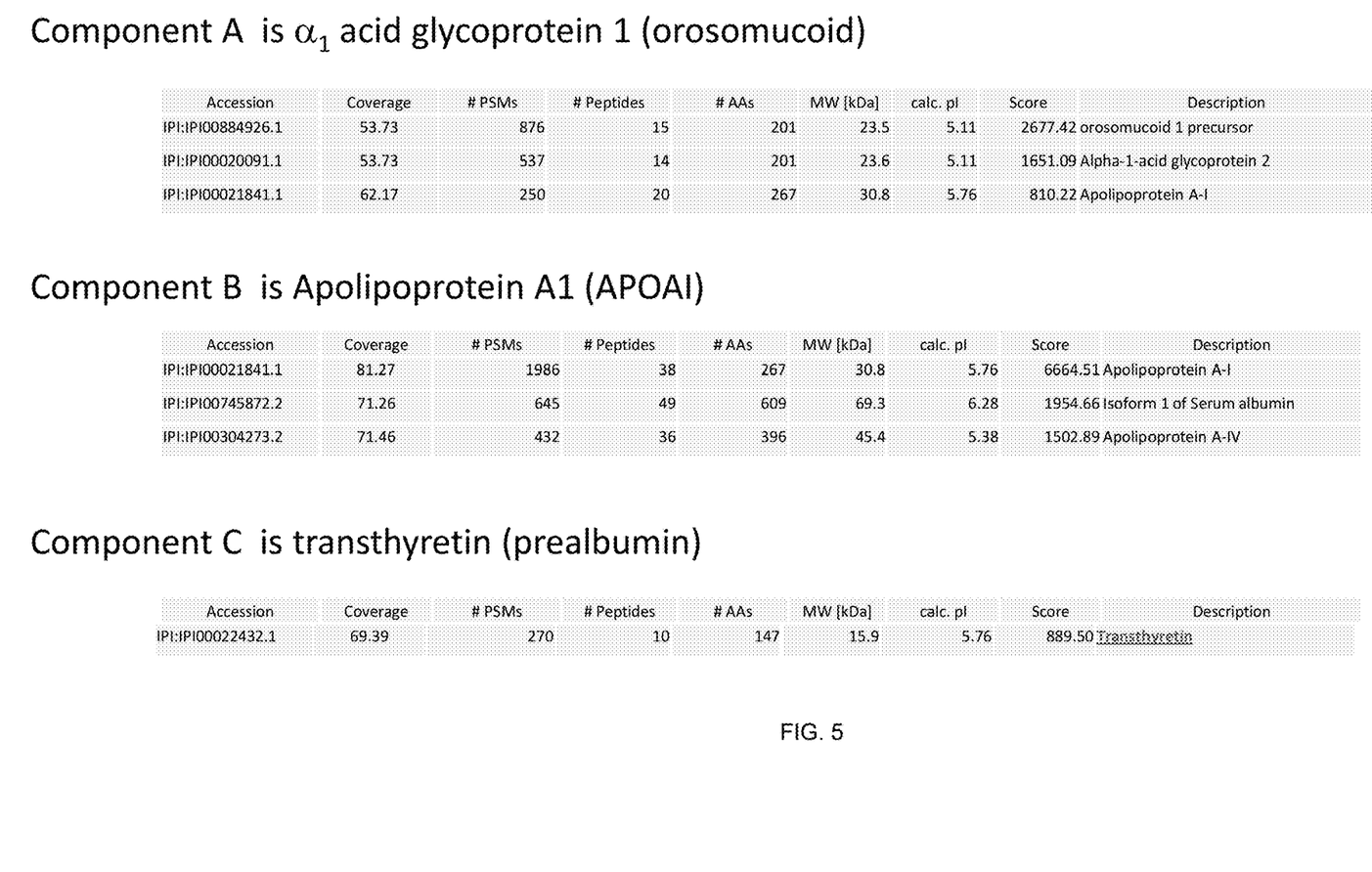
FIG. 5. Identification of proteins in boiled plasma by mass spectrometry. Shown is protein identification data using nano LC/MS-MS.

A sample of boiled plasma (20 μg) was analyzed by SDS-4%-20% gradient polyacrylamide gel electrophoresis, and the separated proteins were visualized by staining with GelCode Blue. Boiled plasma contains three major proteins, designated as component A (~50 kD), component B (~29 kD) and component C (~16 kD), respectively (FIG. 4, lane 1). Commercial preparations of purified a1 acid glycoprotein (5 µg, FIG. 4, lane 2), apolipoprotein A-1 (5 µg, FIG. 4, lane 3), and prealbumin (5 µg, FIG. 4, lane 4) show identical electrophoretic mobility with the three major components in boiled plasma.

Example 6

Identification of Proteins in Boiled Plasma by Mass Spectrometry

Boiled plasma was digested with trypsin (weight ratio 1:20) overnight in the buffer containing 50 mM ammonium bicarbonate and 5% acetonitrile. The resultant peptides were analyzed by nano LC-MS/MS and identified as a1 acid glycoprotein, apolipoprotein A-1, and prealbumin (Table 1). Consistent with these identifications, commercial purified preparations of these three proteins migrated with mobilities similar to components A, B and C in boiled plasma (FIG. 4).

TABLE 1

Identification of proteins in boiled plasma by mass spectrometry (nano LC/MS-MS).

| Accession | Description | Coverage | # Peptides | Score* |
|---|---|---|---|---|
| IPI:IPI00022429.3 | Alpha-1-acid glycoprotein 1 | 42.79 | 12 | 1165.02 |
| IPI:IPI00021841.1 | Apolipoprotein A-I | 81.27 | 38 | 6664.51 |
| IPI:IPI00022432.1 | Transthyretin | 69.39 | 10 | 889.50 |

*Score: this is a probability-based score, which can independently rank the peptides and proteins. The higher the score, the more confidence there is in the protein identification.

Example 7

Figure 6A:
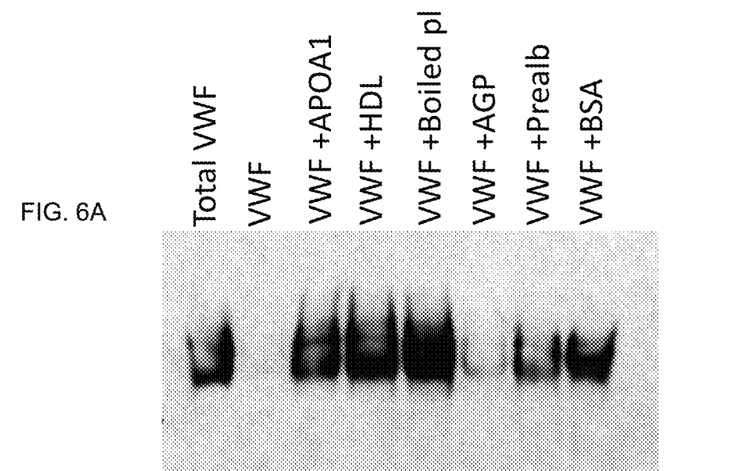
Figure 6B:
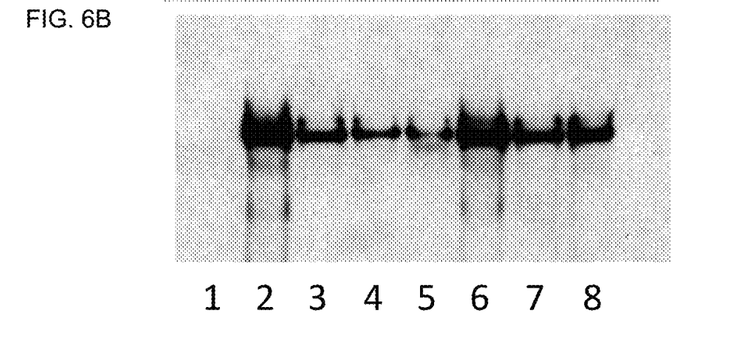

Apolipoprotein A-1 and HDL Prevented Purified Recombinant Biotinylated VWF from Adsorption to Surfaces Purified recombinant biotinylated VWF (6 µg/mL) was incubated for 16 h at 22° C. without and with various proteins and the extent of VWF surface adsorption compared (FIGS. 6A, 6B). Twelve percent of the fluid phase (nonadsorbed) and 12% of the CHAPS-eluted samples (adsorbed) were analyzed by SDS-PAGE and western blotting probed with streptavidin-HRP. Results showed that ApoA-1 (40 µg/mL), HDL (80 µg/ml), and boiled plasma (40 µg/ml), prevented surface-adsorption of VWF (FIG. 6A, lanes 2-5), while a1 acid glycoprotein (40 µg/ml), prealbumin (40 µg/ml), and bovine albumin (40 µg/ml), did not prevent surface-adsorption. These studies showed that ApoA-1 and HDL from commercial sources, purified without the use of heat, were effective in preventing VWF surface adsorption at low concentrations. These results also confirmed that two of the major components in boiled plasma, a1 acid glycoprotein and prealbumin, did not contribute to VWF stabilization, consistent with the hypothesis that ApoA-1 in boiled plasma was the component responsible for stabilizing VWF in solution and preventing its adsorption to surfaces.

Example 8

Figure 7A:
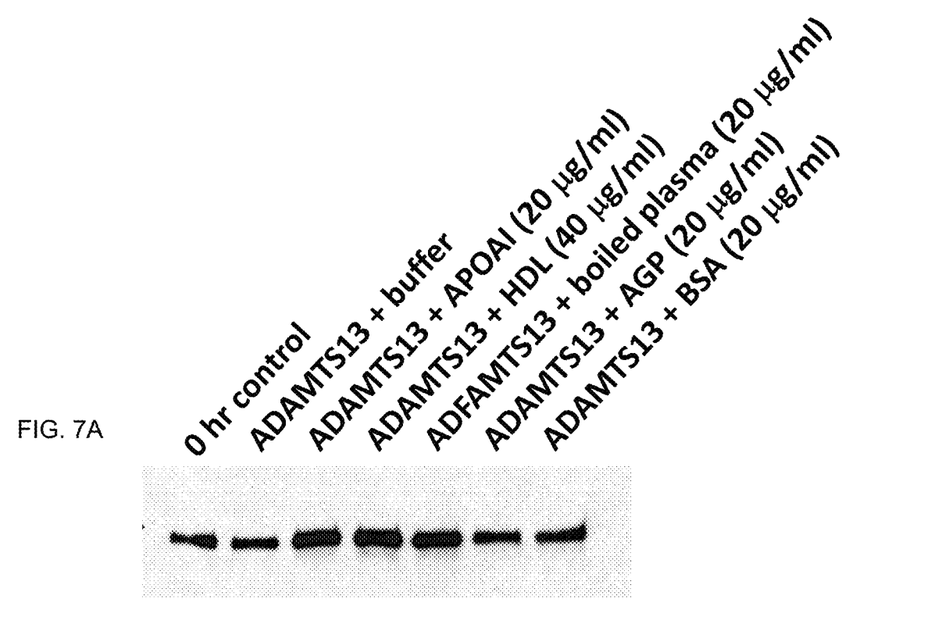
FIG. 7A, ADAMTS13 remaining in solution.
Figure 7B:
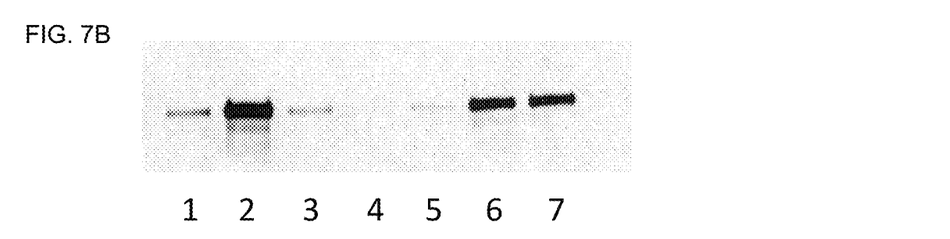
FIG. 7B, ADAMTS13 bound to tube surfaces and eluted in 2% SDS. Lane 1, purified ADAMTS13 before exposure to surface; lane 2, ADAMTS13 after exposure to surface; lane 3, ADAMTS13 with apolipoprotein A-1 (20 µg/mL); lane 4, ADAMTS13 with HDL (40 µg/mL); lane 5, ADAMTS13 with boiled plasma (20 µg/mL); lane 6, ADAMTS13 with a1 acid glycoprotein (20 µg/mL); lane 7, ADAMTS13 with bovine serum albumin (20 µg/mL).

Apolipoprotein A-1 and HDL Prevented Purified Recombinant Biotinylated ADAMTS13 from Adsorption to Surfaces Purified recombinant ADAMTS13 was diluted to 2.6 µg/mL and incubated in microfuge tubes at 22° C. without and with various proteins for 16 hr. Ten percent of the solution was analyzed by SDS-PAGE, western blot, and probed with streptavidin-HRP conjugate. As shown in FIG. 7A, 7B, purified ADAMTS13 adsorbed to the tube surface in the absence of added protein (Lane 2, FIGS. 7A and 7B). Addition of ApoA-1, HDL, and boiled plasma prevented surface-adsorption of ADAMTS13 (Lanes 3-5, FIGS. 7A and 7B), consistent with the interpretation that ApoA-1 in these three preparations prevented surface-adsorption. In comparison, comparable concentrations of a1 acid glycoprotein and albumin failed to prevent surface-adsorption (FIG. 7A, 7B, lanes 6, 7).

Example 9

Figure 8A:
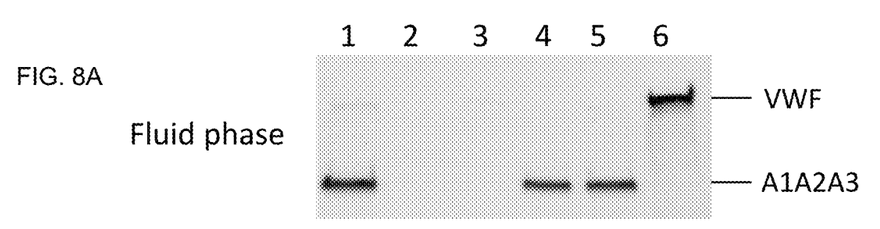
FIG. 8A, biotinylated proteins remaining in fluid phase.
Figure 8B:
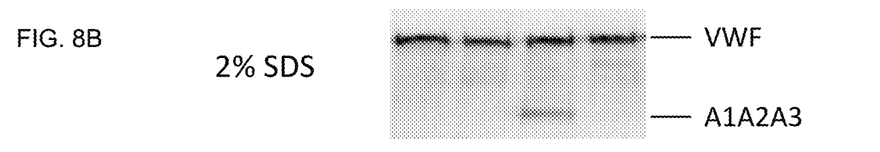
FIG. 8B, biotinylated proteins bound to the surface and eluted in 2% SDS.
Figure 8C:
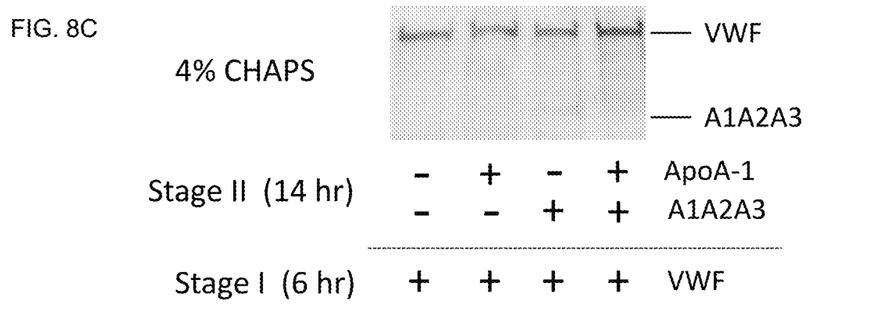
FIG. 8C, biotinylated proteins bound to surface and eluted in 4% CHAPS. Lane 1, purified biotinylated A1A2A3 as reference; lane 2, biotinylated VWF (8 µg/mL) immobilized to tube surface; lane 3, immobilized biotinylated VWF exposed to ApoA-1 (40 µg/mL); lane 4, immobilized biotinylated VWF exposed to purified biotinylated A1A2A3 (8 µg/mL); lane 5, immobilized biotinylated VWF exposed to ApoA-1 (40 µg/mL) and A1A2A3 (8 µg/mL); lane 6, purified biotinylated VWF as reference.

Apolipoprotein A-1 Prevented Association of Purified Recombinant Biotinylated A1A2A3 in the Fluid Phase to Surface-Bound Recombinant Biotinylated VWF The substantial amount of VWF lost to surface adsorption suggests that as fluid-phase VWF molecules are recruited and bind to the immobilized layers of VWF molecules on a limited area on the surface, the newly immobilized molecules must have exposed additional self-association sites to perpetuate the continued capture of VWF molecules in the fluid phase onto the surface. To show that the immobilized VWF surface was able to capture VWF molecules in the fluid phase, we immobilized purified biotinylated VWF to a surface for 6 hr and removed the unbound material from the tubes (Stage I) to produce an immobilized multilayered VWF surface. We confirmed that the immobilized VWF multimers did not dissociate and desorb from the surface when exposed to buffer or ApoA-1 (Stage II) (FIG. 8A, lanes 2, 3). We then exposed the immobilized VWF to a preparation of purified monomeric biotinylated A1A2A3 fragment of VWF (Mr 90 kDa) in the presence or absence of ApoA-1 (Stage II). Subsequent elution with SDS and CHAPS showed that a portion of the monomeric biotinylated A1A2A3 fragment in the fluid phase had bound to the immobilized VWF exclusively via protein-protein (i.e. VWF-A1A2A3) interactions (FIG. 8B, lane 4), while the presence of ApoA-1 blocked this interaction (FIG. 8B, lane 5). These results showed that the biotinylated VWF-coated surface formed in Stage I was able to further recruit and bind a monomeric VWF fragment in the fluid phase during stage II. No biotinylated A1A2A3 was eluted by 4% CHAPS (FIG. 8C, lanes 4, 5), indicating that the biotinylated A1A2A3 did not bind directly to the tube surface through hydrophobic interactions. These results confirmed that after a fluid-phase VWF molecule has bound to and become a part of the immobilized VWF, it changed its conformation and exposed new self-association site(s), and continued to recruit other fluid-phase VWF molecules, including a monomeric VWF fragment, onto the immobilized VWF and this process of self-association was interrupted by the presence of ApoA-1.

Example 10

Figure 9A:
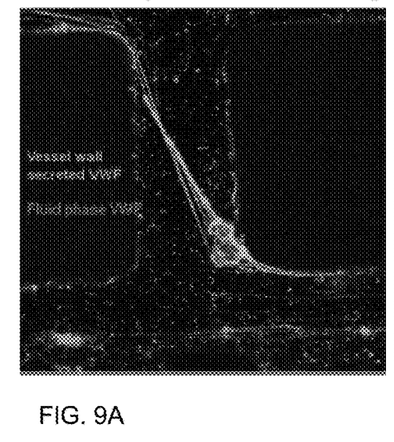
FIGS. 9A, 9B. Fluid-phase VWF attachment to transluminal fiber. Shown is the process of VWF self-association in endothelialized synthetic microvessels.
Figure 9B:
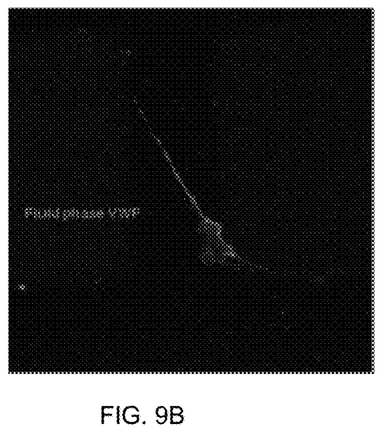
Figure 10A:
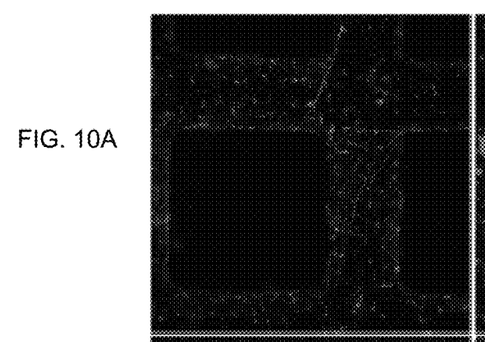
FIGS. 10A-10D. ApoA-1 blocks soluble VWF binding to ULVWF fibers. Shown is the effect of Apo-A1 perfusion through endothelialized synthetic microvessels prior to the perfusion of biotinylated soluble VWF on VWF self-association.
Figure 10B:
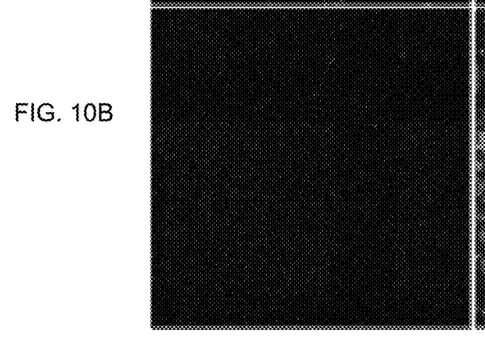
Figure 10C:
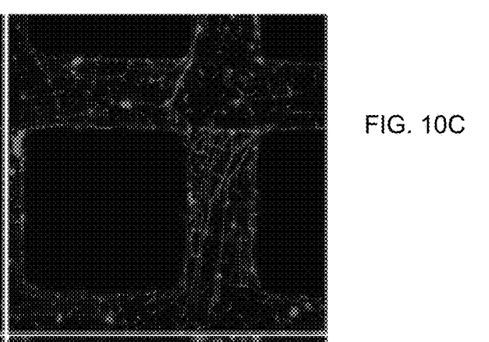
Figure 10D:
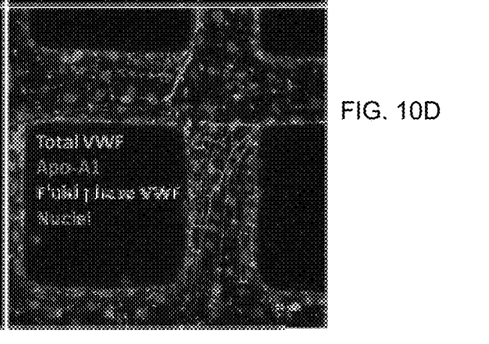

Apolipoprotein A-1 Prevented the Association of VWF in Solution to Immobilized ULVWF Fibers We studied the effect of ApoA-1 in VWF self-association in endothelialized synthetic microvessels according to the method of Zheng et al (PNAS 109:9342-9347, 2012). When we stimulated the endothelial cells in the synthetic microvessels with phorbol myristate acetate (PMA), endothelial cells secreted VWF molecules from the Weibel-Palade bodies. The secreted VWF molecules form macroscopic transluminal ULVWF fibers (FIG. 9A). When we perfused soluble biotinylated VWF multimers through these microvessels, we observed that the biotinylated VWF molecules bound to the ULVWF fibers (FIG. 9B). However, when Apo-A1 was perfused through the vessels prior to the biotinylated soluble VWF, no association of soluble VWF with the ULVWF fibers was observed (FIG. 10B). This result shows that ApoA-1 can inhibit the recruitment of circulating VWF to the transluminal ULVWF fibers under flow. We immuno-stained the fixed microvessels after perfusion of ApoA-1, and verified that ApoA-1 had bound to the ULVWF fibers (FIG. 10C). This result confirmed that ApoA-1 binding to the ULVWF fibers completely prevented the association of soluble VWF to the ULVWF fibers. Since the transluminal ULVWF fibers have been exposed to 6% albumin prior to perfusion of ApoA-1 or soluble VWF, the binding of ApoA-1 or soluble VWF to the ULVWF fibers was specific. The lack of soluble VWF associating with ApoA-1-saturated ULVWF fibers also showed soluble VWF was unable to displace the ApoA-1 that had bound to the ULVWF fibers, suggesting that ApoA-1 had a higher affinity for the ULVWF fibers than soluble VWF.

Example 11

HDL Decreases VWF Release and Modulates VWF Self-Association into ULVWF Strings

Figure 11A:
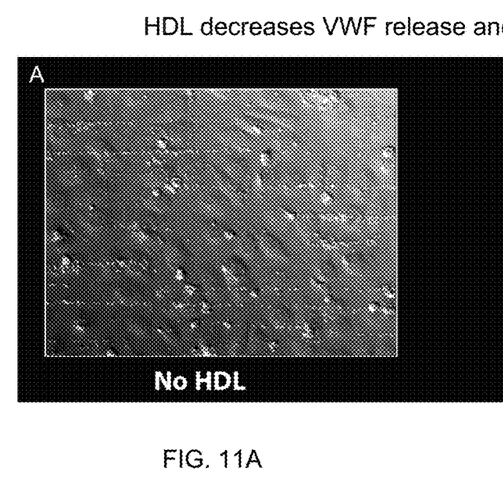
FIGS. 11A-11C. HDL decreases VWF release and modulates ULVWF assembly. Shown is the effect of HDL on VWF release from activated endothelial cells and on modulation of VWF self-assembly into ULVWF strings.
Figure 11B:
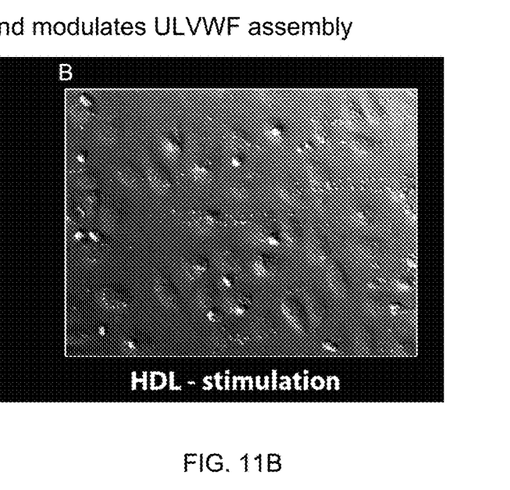
Figure 11C:
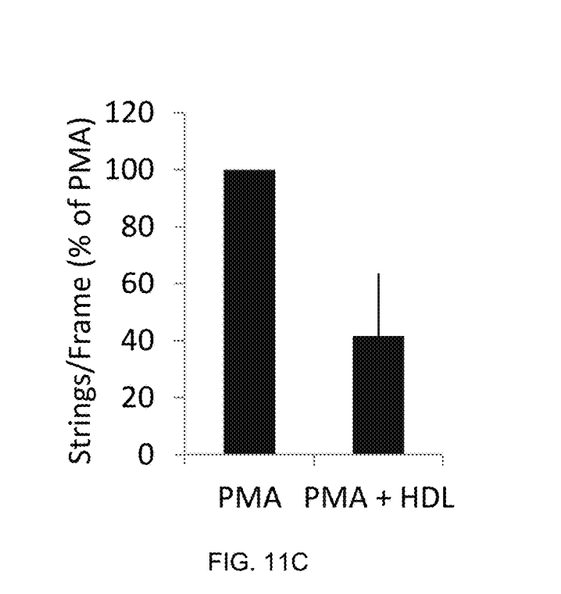

We stimulated endothelial cells grown in flow chambers with PMA in the presence or absence of HDL. The secreted VWF was detected by binding of fixed platelets. There were fewer and shorter platelet-decorated ULVWF strings on the endothelial cells stimulated in the presence of HDL than those stimulated in the absence of HDL (FIGS. 11A-11C). This result shows that HDL reduces VWF release from activated endothelial cells and consequently modulates VWF self-assembly into ULVWF strings.

VWF secreted from the endothelium can form large fibers that self-associate, trap platelets, and can cause microvascular occlusion. Apo-A1 decreases VWF release, modulates fiber self-association, and prevents association of fluid-phase VWF with endothelial VWF. We postulate that the apoA1 level determines the extent of pathology caused by syndromes with activation of the microvasculature: TTP, HUS, sepsis, malaria, sickle cell disease. HDL, ApoA1 or synthetic peptides derived from it could be used as an adjunct to treat these disorders.

It will be readily apparent to one of ordinary skill in the relevant arts that other suitable modifications and adaptations to the methods and applications described herein are suitable and can be made without departing from the scope of the invention or any aspect thereof. While the invention has been described in connection with certain aspects, it is not intended to limit the invention to the particular forms set forth, but on the contrary, it is intended to cover such alternatives, modifications and equivalents as can be included within the spirit and scope of the invention as defined by the following claims.

All references, issued patents, and patent applications cited within the body of the specification are hereby incorporated by reference in their entirety, for all purposes.

The invention claimed is:

1. A composition comprising:
   an in vitro protein selected from the group consisting of Von Willebrand Factor (VWF), Factor VIII, ADAMTS13, and Factor IX;
   an amount of (i) Apolipoprotein A1 (ApoA-1), (ii) high density lipoprotein (HDL), or (iii) ApoA-1 and HDL, sufficient to reduce or prevent loss of the in vitro protein by adsorption of the in vitro protein to an in vitro surface or by self-association; and
   a transport fluid or a flush solution, wherein the transport fluid or the flush solution comprises a 4-(2-hydroxyethyl)-1-piperazineethanesulfonic acid (HEPES) buffer or ethylenediamine tetraacetic acid (EDTA).

2. The composition of claim 1, wherein the in vitro protein is a recombinant purified protein.

3. The composition of claim 1, wherein the in vitro protein is non-recombinant.

4. The composition of claim 1, wherein the in vitro protein is a human protein.

5. The composition of claim 1, wherein the in vitro protein is VWF.

6. The composition of claim 5, wherein the VWF is a VWF fragment corresponding to a processed VWF fragment selected from the group consisting of: a proteolytically cleaved VWF fragment, a furin processed VWF fragment, an ADAMTS13 processed VWF fragment, and a thrombospondin-1 processed VWF fragment.

7. The composition of claim 5, wherein the VWF is a VWF fragment corresponding to a A1A2A3 region of VWF.

8. The composition of claim 1, wherein the in vitro protein is Factor VIII.

9. The composition of claim 1, wherein the in vitro protein is ADAMSTS13.

10. The composition of claim 1, wherein the in vitro protein is Factor IX.

11. The composition of claim 1, wherein the concentration of ApoA-1, if present, is at least 40 µg/mL, and the concentration of HDL, if present, is at least 80 µg/mL.

12. The composition of claim 1, wherein the composition comprises ApoA-1 but not HDL.

13. The composition of claim 1, wherein the amount of ApoA-1, HDL, or ApoA-1 and HDL is in a coating on a glass or plastic in vitro surface.

14. The composition of claim 1, wherein the amount of ApoA-1, HDL, or ApoA-1 and HDL is in a coating on an in vitro medical device surface.

15. The composition of claim 14, wherein the in vitro medical device surface is a surface of an in vitro catheter, port, or ventricular assist device.

16. The composition of claim 1, wherein the amount of ApoA-1, HDL, or ApoA-1 and HDL is in a coating on an interior surface of a container holding the composition.

17. The composition of claim 1, wherein the amount of ApoA-1, HDL, or ApoA-1 and HDL is in a coating on an in vitro synthetic microvessel surface.

18. The composition of claim 1, wherein the amount of ApoA-1, HDL, or ApoA-1 and HDL is sufficient to reduce or prevent loss of the in vitro protein by adsorption of the in vitro protein to the in vitro surface.

19. The composition of claim 1, wherein the amount of ApoA-1, HDL, or ApoA-1 and HDL is sufficient to reduce or prevent loss of the in vitro protein by self-association.

\* \* \* \* \*